(12) United States Patent
Fish et al.

(10) Patent No.: US 6,289,829 B1
(45) Date of Patent: Sep. 18, 2001

(54) PLANTING APPARATUS WITH IMPROVED LIQUID PESTICIDE DELIVERY DEVICE AND RELATED METHOD FOR DELIVERING LIQUID PESTICIDE

(75) Inventors: James D. Fish, Raleigh, NC (US); Timothy J. Bender, Milton, WI (US); David A. Feist, Batavia, IL (US); Grant E. Splear, Coralville, IA (US)

(73) Assignee: Aventis CropScience S.A., Lyons (FR)

( * ) Notice: Subject to any disclaimer, the term of this patent is extended or adjusted under 35 U.S.C. 154(b) by 0 days.

(21) Appl. No.: 09/396,332

(22) Filed: Sep. 15, 1999

Related U.S. Application Data (60) Provisional application No. 60/100,806, filed on Sep. 18, 1998, and provisional application No. 60/100,805, filed on Sep. 18, 1998.

(51) Int. Cl.$^7$ ............................................. A01C 23/00
(52) U.S. Cl. ............................ 111/121; 111/127; 111/150
(58) Field of Search ............................ 111/113, 119–126, 111/161, 170, 190, 139, 191, 194, 197, 198, 127, 150, 157

(56) References Cited

U.S. PATENT DOCUMENTS

| | | | |
|---|---|---|---|
| 3,632,043 | * | 1/1972 | Kirschmann ........................ 239/146 |
| 3,745,944 | * | 7/1973 | Yetter et al. ........................ 172/657 |
| 3,863,842 | * | 2/1975 | McGarland et al. ................. 239/283 |
| 4,253,412 | * | 3/1981 | Hogenson ............................. 111/86 |
| 4,638,748 | * | 1/1987 | Kopecky ................................ 111/7 |
| 4,669,922 | | 6/1987 | Hooper et al. . |
| 4,674,419 | * | 6/1987 | Kopecky .............................. 111/73 |
| 4,711,187 | * | 12/1987 | Schultz .................................. 111/7 |
| 5,092,255 | * | 3/1992 | Long et al. .......................... 111/167 |
| 5,425,318 | | 6/1995 | Keeton . |
| 5,460,106 | * | 10/1995 | Crockett et al. ..................... 111/127 |
| 5,640,915 | | 6/1997 | Schaffert . |
| 5,752,453 | * | 5/1998 | Nikkel et al. ....................... 111/121 |
| 5,862,763 | * | 1/1999 | Dietrich, Sr. ....................... 111/121 |
| 6,029,590 | * | 2/2000 | Arriola et al. ..................... 111/124 |
| 6,038,990 | * | 3/2000 | Simpson ............................. 111/124 |

* cited by examiner

*Primary Examiner*—Victor Batson
(74) *Attorney, Agent, or Firm*—Jenkins & Wilson, P.A.

(57) ABSTRACT

A planting machine for delivering liquid pesticides to the soil mixing zone preceding the furrow closing mechanism to effectively distribute liquid pesticide throughout soil covering seed in a furrow. The planting machine has a furrow opening mechanism, seed dispensing means, and furrow closing mechanism and includes a seed positioning means mounted on the seed dispensing means for effectively locating seeds in the furrow. Also, the planting machine includes means for liquid pesticide spray delivery mounted thereon so as to direct a spray towards the furrow closing mechanism and into the soil mixing zone being created by the furrow closing mechanism. The means for spray delivery can be mounted on the conventional seed positioning means as well as independently mounted on the planting machine.

13 Claims, 9 Drawing Sheets

PLANTING APPARATUS WITH IMPROVED LIQUID PESTICIDE DELIVERY DEVICE AND RELATED METHOD FOR DELIVERING LIQUID PESTICIDE

This application claim benefit to provisional application 60/100,806 filed Sep. 18, 1998, which also claim benefit to provisional 60/100,805 filed Sep. 18, 1998.

TECHNICAL FIELD

The present invention relates to methods of delivering pesticides with agricultural seed planters, and more particularly to agricultural seed planters which include liquid pesticide delivery apparatus.

RELATED ART

Multi-row planters and drills are conventionally used for agricultural seed planting. Each planter and drill includes multiple row units adapted for opening a seed furrow, depositing seeds within the seed furrow, and closing the seed furrow around the seeds. Additionally, it is well known to those skilled in the art to utilize a variety of attachments, including liquid and granular pesticide delivery devices, in combination with the row units.

It is also well known that for optimum seed germination, seed must be placed at the proper soil depth in the furrow, where the seed will receive the correct moisture and temperature. The seed is dropped from a planter into a furrow through a seed tube, and the seed tube is designed and positioned on the planter to drop the seed into the bottom of the furrow. However, as seeds pass through the seed tube, they are prone to bouncing which effects the direction at which they leave the seed tube and fall into the furrow. Further, seeds being planted many times bounce off of the soil when dropped into the seed furrow because of the speed with which they drop to the ground. If seeds are improperly positioned in a furrow, the seeds are in turn likely to be covered by an inadequate layer of soil that will adversely affect many growth aspects of the resulting plant. For example, improper seed placement in the furrow and resulting improper soil coverage of the seed can result in uneven plant emergence, for instance, increased weed population, non-uniform maturity, longer insect life cycles, higher susceptibility to chemical damage, and ultimately lower yields.

The prior art discloses many attempts to address the aforementioned problems. Several well known devices include the KEETON® seed firming attachment disclosed in U.S. Pat. No. 5,425,318 (assigned to J & K Keeton Enterprises, Inc.); and the REBOUNDER™ device disclosed in U.S. Pat. No. 5,640,915 and manufactured by Schaffert Manufacturing Company, Inc. The KEETON® seed firmer disclosed in U.S. Pat. No. 5,425,318 attaches to the seed tube and applies pressure to the seed to assure proper positioning in a furrow. Similarly, the REBOUNDER™ device manufactured by Schaffert Manufacturing Company, Inc. is attached to the seed tube and attempts to properly position seeds in the furrow by reducing seed bounce for proper placing of seeds in a furrow. Other similar attempts to control seed bounce and/or otherwise improve seed positioning in a furrow are disclosed in U.S. Pat. Nos. 5,092,255 to Long et al.; 4,669,922 to Hooper et al.; and 4,253,412 to Hogenson.

More directly relating to the present invention, it is desirable to properly apply a pesticide in the seed furrow during planting to achieve optimal seed and plant protection. The present invention addresses a device and method for applying liquid pesticide, e.g., insecticide, to a seed furrow during planting.

Figure 1:
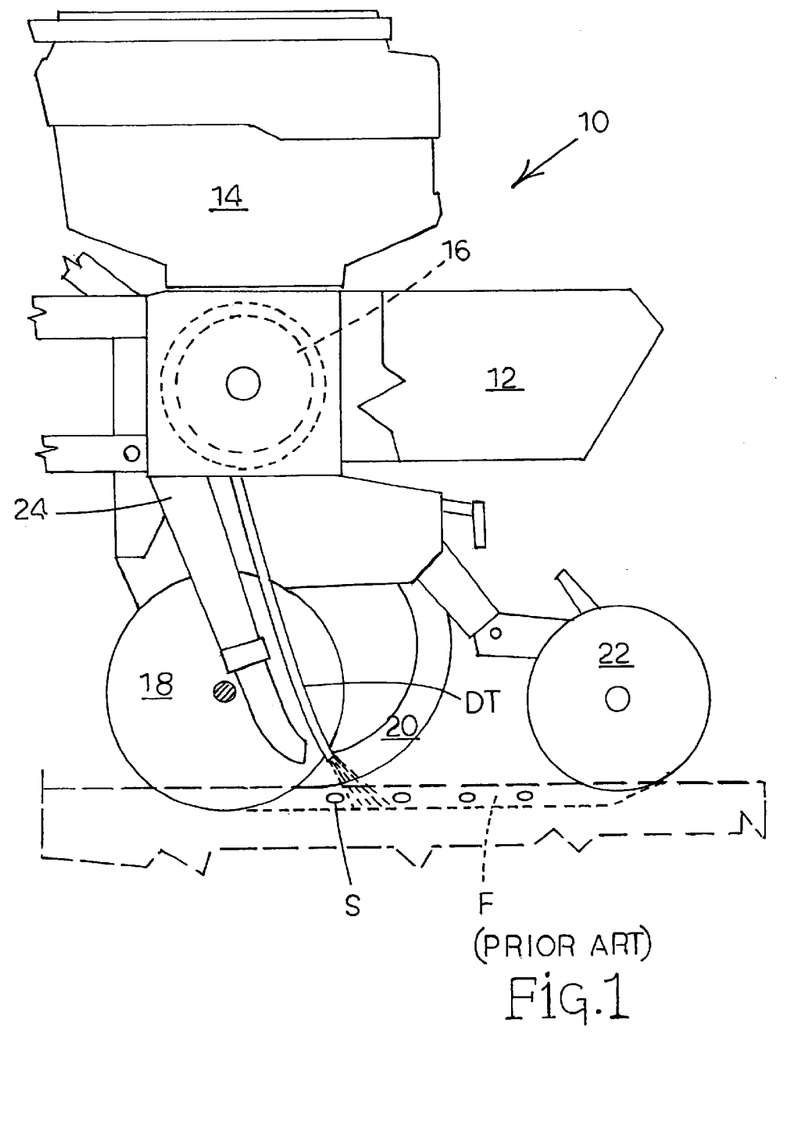
FIG. 1 is a side elevation view of a prior art "drop tube" planting machine.

It is known that liquid pesticides may be applied by a planting machine by means of a drop tube connected to the seed tube or by means of a spray nozzle positioned between the seed tube and furrow closing wheel of a planting machine wherein the planting machine does not incorporate a seed firmer or REBOUNDER™ device for properly positioning seed within a furrow. FIG. 1 shows the "drop-tube" type of planting machine. The drop tube DT, which is optionally attached to the seed tube, administers a dost of pesticide composition in the bottom of the furrow and on the seed which results in the placement of the pesticide as in FIG. 8A. If the liquid pesticide composition is sprayed into the bottom of a seed furrow or onto the seed itself, the liquid pesticide, particularly the insecticide, located below or around the seed may not serve to protect the ball-like root structure above the seed from soil-borne pests such as western rootworm.

Figure 2:
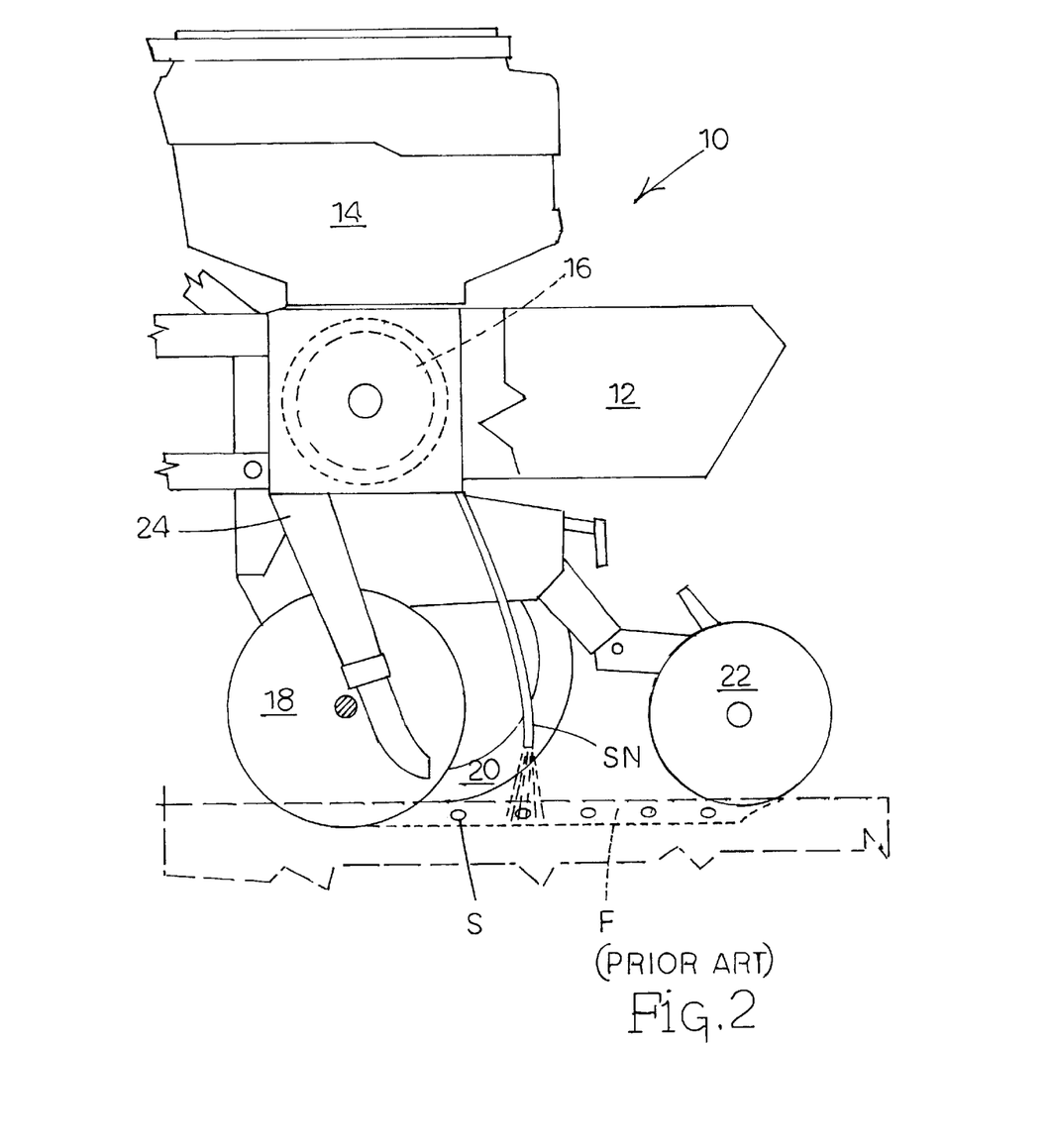
FIG. 2 is a side elevation view of a prior art "in-furrow spray nozzle" planting machine.
Figure 9A:
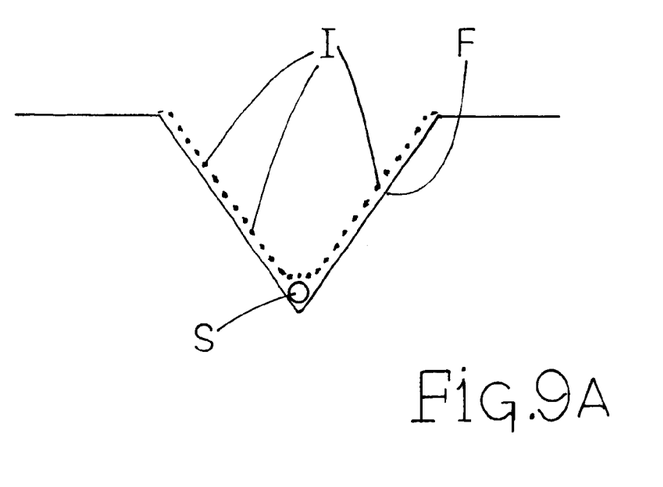
FIGS. 9A and 9B are vertical cross-sectional views illustrating application of liquid pesticide to a seed within a furrow by the prior art device of FIG. 2 before and after closure of the furrow, respectively.
Figure 9B:
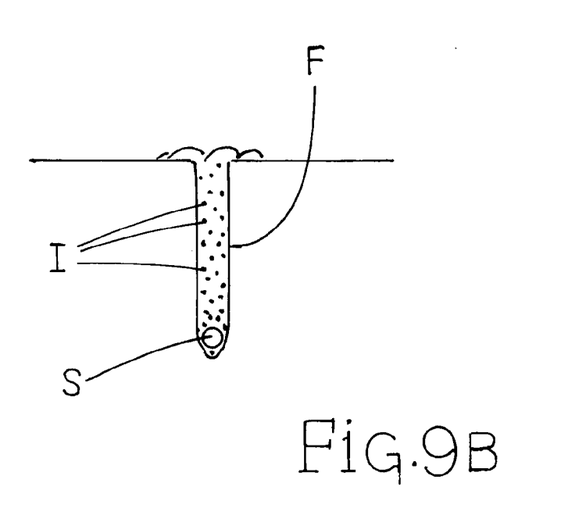

FIG. 2 shows an in-furrow spray nozzle type applicator. The spray nozzle SN applies a high volume (4–7 gallons per acre) spray of pesticide on the seed and the soil around it which provides a "T-band" application of pesticide in the furrow on the seed and over the seed so planted after the furrow is closed. FIG. 9A exemplifies the pesticide distribution on the soil and seed before the furrow is closed; FIG. 9B exemplifies the distribution after the furrow is closed. Liquid pesticides, particularly liquid insecticides, are better distributed in this type of "T-band" when the application is effected at high volumes of liquid per unit land area, e.g., 4 to 20 gallons per acre (55 to 225 L/Ha).

The T-band application as described in FIG. 2 also provides an application of the pesticide on the top of the soil since it is very difficult to keep the pesticide completely contained in the furrow at high volumes. This is generally disadvantageous since the pesticide may be transported by wind or runoff from rainfall.

Generally, in-furrow applications of pesticides in corn are effected by placement of granules comprising a pesticide in the furrow. Applications of liquid pesticides are generally not used for the control of corn rootworms. Applicants have overcome the shortcomings of the prior art application of liquid pesticide by a planting machine by means of the apparatus and method described hereinafter.

An object of the present invention is to provide a method of applying pesticidal compositions in a furrow.

Another object of the present invention is to provide a method of applying liquid pesticidal compositions in a furrow.

Another object of the present invention is to provide a method of applying liquid pesticidal compositions in a furrow at low volumes of liquid per unit land area.

Another object of the present invention is to provide an improved method of applying pesticides in corn.

Another object of the present invention is to provide an improved method of controlling soil-borne pests in corn.

Another object of the present invention is to provide an improved method of controlling soil-borne pests in corn in the early part of the growing season.

These objects are met in whole or in part by the present invention.

DISCLOSURE OF THE INVENTION

The present invention provides a method of application of liquid pesticide to a seed furrow created by a planting assembly having a furrow opening mechanism, a seed dispensing means including a seed tube for directing the seeds downwardly and rearwardly as the planting assembly moves forward, and a furrow closing mechanism that creates a soil mixing zone in front of the leading edge of the furrow closing mechanism, the method comprising the steps of directing liquid pesticide spray into the soil mixing zone in front of the furrow closing mechanism and covering seed in the seed furrow with soil comprising the mixture of soil and liquid pesticide spray. In this way a mixture of soil and pesticide is created in the soil mixing zone.

In a highly preferred embodiment of the present invention, the planting assembly further comprises a spray delivery means which directs the pesticide into the soil mixing zone. The spray delivery means may be a drop tube, spray nozzle, or other such structure known to those skilled in the art, a very highly preferred embodiment of which is described infra.

The spray of the pesticide is generally directed into the soil mixing zone below the level of the top of the furrow. In this way, applicants have found that the pesticide is incorporated in the soil below the level of the soil as the furrow is closed. The application spray can be a stream of liquid or a conical spray.

Generally the volume of liquid to be used per unit land area is from 0.1 to 50 gallons per acre, preferably from 0.2 to 10, more preferably from 0.5 to 5, most preferably from 1 to 3 gallons per acre. The volume per unit may also be varied with the forward speed of the assembly or may be varied by a pressure means.

In a highly preferred embodiment of the invention, the pesticidal composition is applied when the soil temperature is from 4° C. to 25° C., preferably from 10° C. to 20° C. In this way there is a better control of soil-bome insect species than when the composition is deposited directly on the seed as in the method of the prior art.

The liquid pesticide spray is generally a liquid composition comprising one or more pesticides. Generally the pesticide is an insecticide or a fungicide. The liquid composition is generally an aqueous composition into which has been mixed a concentrated pesticidal composition, e.g., an emulsifiable concentrate, a suspension concentrate, an aqueous emulsion, a wettable powder, or another pesticidal composition known to the skilled worker.

In a highly preferred embodiment, the liquid composition may be applied as a mixture with a fertilizer, more preferably a pop-up fertilizer.

When the pesticide is an insecticide, the pesticide may be:

(a) an organophosphate insecticide, for example, chlorpyrifos, chlorethoxyfos, terbufos or terbupirimfos;

(b) an N-methylcarbamate insecticide, for example, carbofuran;

(c) a pyrethroid insecticide, for example, tefluthrin, permethrin, fenvalerate, esfenvalerate, cypermethrin, cyhalothrin, lambda-cyhalothrin, bifenthrin or deltamethrin; or (d) an insecticidal 1-aryl pyrazole.

Generally the preparation and formulations of the above insecticides may be found in *The Pesticide Manual,* 11th edition, C. D. S. Tomlin, editor, British Crop Protection Council, 1997. The rates of the above insecticides may be found by consulting the labels on the products themselves. Advantageously, the rates recommended in the prior art may be optionally lowered by the use of the method of the present invention.

If the insecticide is an insecticidal 1-arylpyrazole, it is preferably a compound of formula (I)

wherein:

$R_1$ is CN or methyl;

$R_2$ is $S(O)_nR_3$;

$R_3$ is alkyl or haloalkyl;

$R_4$ is selected from the group comprising a hydrogen atom, a halogen atom, and a radical which may be $—NR_5R_6$, $C(O)OR_7$, $—S(O)_mR_7$, alkyl, haloalkyl, $—OR_8$, or $—N{=}C(R_9)(R_{10})$; $R_4$ is preferably an amino group, which is unsubstituted or which bears one or two substituents selected from the group consisting of alkyl, haloalkyl, acyl and alkoxycarbonyl;

$R_5$ and $R_6$ are independently selected from a hydrogen atom, alkyl, haloalkyl, —C(O)alkyl, $—S(O)_rCF_3$; or $R_5$ and $R_6$ form together a divalent radical which may be interrupted by one or more heteroatoms;

$R_7$ is selected from alkyl or haloalkyl;

$R_8$ is selected from alkyl, haloalkyl or the hydrogen atom;

$R_9$ is selected from the hydrogen atom and alkyl;

$R_{10}$ is selected from phenyl or heteroaryl that is optionally substituted by one or more hydroxy, a halogen atom, —O-alkyl, —S-alkyl, cyano, or alkyl or combinations thereof;

X is selected from the Nitrogen atom and the radical $C—R_{12}$;

$R_{11}$ and $R_{12}$ are independently selected from a halogen atom or the hydrogen atom;

$R_{13}$ is selected from a halogen atom, haloalkyl, haloalkoxy, $—S(O)_qCF_3$, $—SF_5$, preferably from a halogen atom, haloalkyl, haloalkoxy, $—SF_5$;

m, n, q, r, are independently selected from 0, 1, and 2;

provided that when $R_1$ is methyl, $R_3$ is haloalkyl, $R_4$ is $NH_2$, $R_{11}$, is Cl, $R_{13}$ is $CF_3$, and X is N.

The alkyl and alkoxy groups of the formula (I) are preferably lower alkyl and alkoxy groups, that is, radicals having one to four carbon atoms. The haloalkyl and haloalkoxy groups likewise preferably have one to four carbon atoms. The haloalkyl and haloalkoxy groups can bear one or more halogen atoms; preferred groups of this type include $—CF_3$ and $—OCF_3$.

The preparation of compounds of formula (I) can be effected according to any process described in International Patent Publication Nos. WO 87/03781, WO 93/06089 and WO 94/121606, as well as in European Patent Publication Nos. 0295117, 0403300, 0385809, and 0679650, German Patent Publication No. 19511269 and U.S. Pat. Nos. 5,232,940 and 5,236,938.

Preferably the compound of formula (I) has one or more of the following features:

$R_1$ is CN;

$R_4$ is —$NR_5R_6$;

$R_5$ and $R_6$ are independently selected from the hydrogen atom, alkyl, haloalkyl, —C(O)alkyl, C(O)$OR_7$;

X is C—$R_{12}$; or $R_{13}$ is selected from a halogen atom, haloalkyl, haloalkoxy, or —$SF_5$.

Most preferably the compound of formula (I) is 5-amino-3-cyano-1-(2,6-dichloro -4-trifluoromethyl)phenyl-4-trifluoromethylsulfinylpyrazole (or fipronil) or 5-amino-3-cyano-1-(2,6-dichloro-4-trifluoromethylphenyl)-4-ethylsulfinylpyrazole hereinafter known as Compound B.

BEST MODE FOR CARRYING OUT THE INVENTION

While applicants contemplate that the device and method of the present invention can be used with many different types of planters and drills, it will be described herein for convenience as used with a double-disk furrow opener style planter as described in detail below and as shown in the drawings.

In accordance with the present invention, applicants provide a planting assembly having a furrow opening mechanism, a seed dispensing means including a seed tube for directing the seeds downwardly and rearwardly as the planting assembly moves forward, and a furrow closing mechanism that creates a soil mixing zone in front of the leading edge thereof. The assembly comprising: a means for liquid pesticide spray delivery mounted on the planting assembly and adapted to direct a spray towards the furrow closing mechanism and into the soil mixing zone being created by the furrow closing mechanism. The planting assembly optionally includes a seed guiding and positioning means mounted on the seed tube for effectively placing seed at a substantially consistent depth and good spacing in the furrow.

Applicants' novel liquid pesticide delivery device and method are optionally intended for use in combination with a planting machine utilizing a seed firmer or REBOUNDER™ device for proper positioning of seeds within a furrow. The combination of proper positioning of seeds within a furrow by a seed firmer or REBOUNDER™ device as disclosed in the prior art in combination with applicants' novel liquid pesticide delivery device provides for optimal positioning of a liquid pesticide such as fipronil in the furrow soil surrounding a seed.

Figure 3:
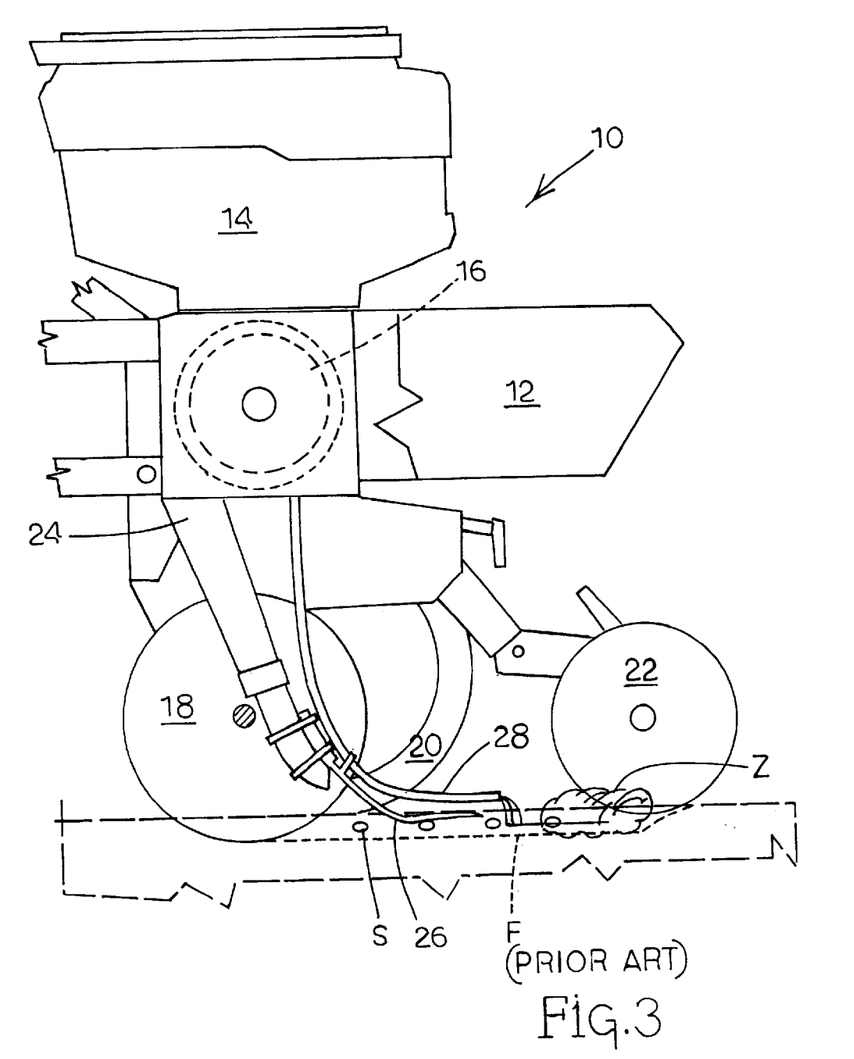
FIG. 3 is a side elevation view of a prior art planting machine with a REBOUNDER™ seed control device (with liquid microtube) that is affixed to the seed tube.

Referring now to the drawings, there is shown in FIGS. 1–7 a seed planting machine 10 that is drawn across a field in a forward direction as is known to one skilled in the art. Planting machine 10 generally includes a main frame 12 that serves to support a seed hopper 14, a seed metering unit 16 which receives kernels from seed hopper 14, a furrow opening device 18, a gauge wheel assembly 20 pivotally connected to main frame 12 and providing various planting positions with respect to furrow opening device 18. A furrow closing device 22 is provided which serves to cover seeds in furrow F with soil, and a seed tube 24 which receives seed S from seed metering unit 16 and directs seed S into open furrow F. A REBOUNDER™ seed cover that serves to guide and position seed S in furrow F is shown in FIG. 3 attached to the end of seed tube 24 in a well known manner (as can be seen in FIG. 2 of U.S. Pat. No. 5,640,915 to Schaffert referenced above). The REBOUNDER™ extension is also shown in FIG. 3 as having conventional pesticide tube 28 attached by bracket thereto for applying liquid fertilizer to seed S in a well known manner and as clearly shown in FIG. 26 of U.S. Pat. No. 5,640,915 to Schaffert. The prior art REBOUNDER™ extension 26 and attached liquid pesticide tube 28 shown in FIG. 3 merely provide for the application of liquid pesticide I directly over the top of seed S after the seeds have come to rest in furrow F prior to the furrow being closed by furrow closing device 22. The liquid pesticide application over the top of seed S can best be seen with reference to FIG. 8A of the drawings.

Figure 4:
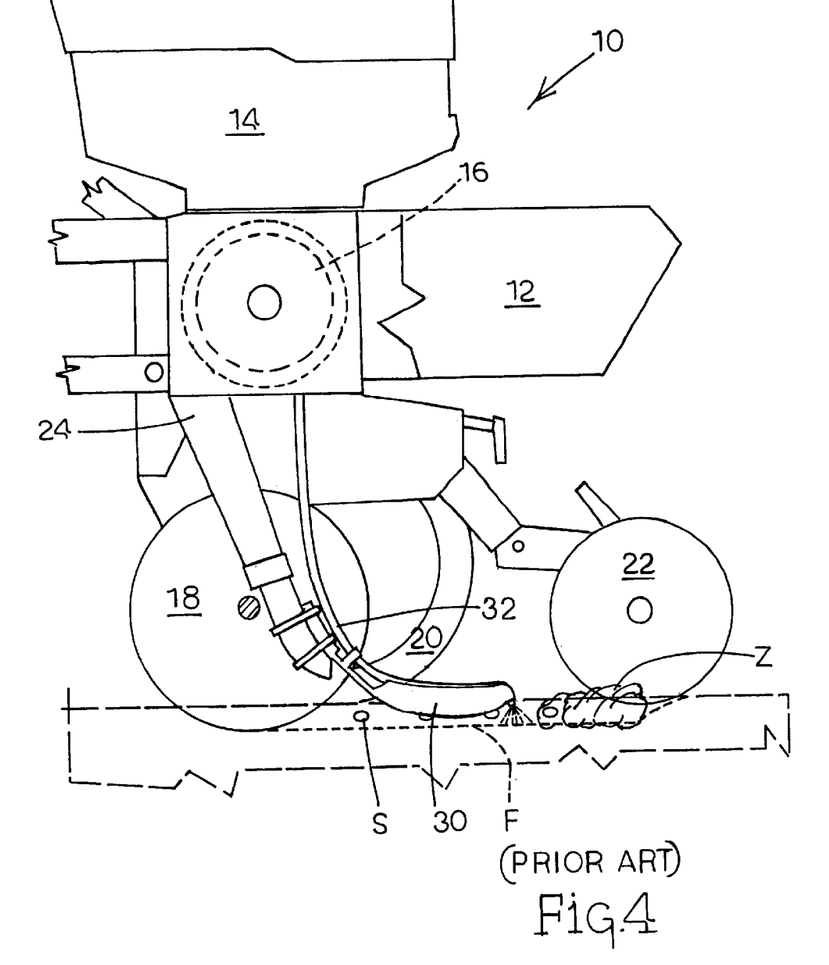
FIG. 4 is a side elevation view of a prior art planting machine with a KEETON® seed firmer device (with liquid microtube) that is affixed to the seed tube.

FIG. 4 discloses a similar planting machine 10 having a KEETON® seed firmer 30 attached to the bottom of seed tube 24 which is biased against the soil and furrow F in a position trailing seed tube 24 to facilitate applying force to seed S to firm seed S into the soil at a desired planting depth. KEETON® seed firmer 30 is also provided with a known microtube 32 that extends along the length thereof and is directed downwardly at its lowermost end to provide liquid pesticide over the top of seed S passing thereunder. Referring now to FIG. 8B of the drawings, the efficacy of prior art seed firmer 30 with liquid pesticide microtube 32 for pesticide delivery can be seen wherein a shallow coating of pesticide I is provided around the circumference of seed S. Unfortunately, neither the prior art device of FIG. 3 nor the prior art device of FIG. 4 serves to deliver an adequate liquid pesticide coating above seed S since liquid pesticide I is in the bottom of the furrow either on top of or around seed S so that when roots grow in a ball around seed S, the roots above the seed will be subject to attack by rootworms and the like.

Figure 5:
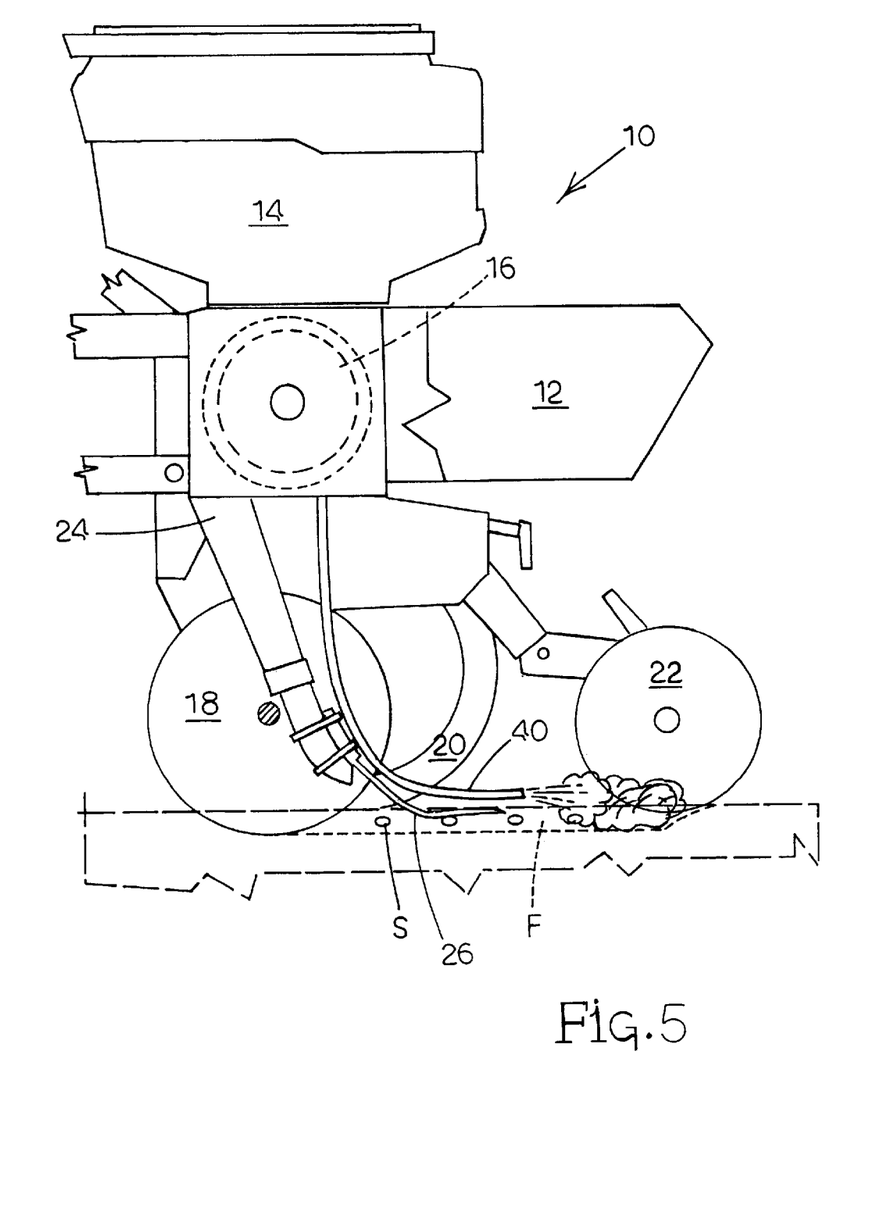
FIG. 5 is a side elevation view of a planting machine with a REBOUNDER™ seed control device being provided with a novel liquid pesticide delivery device.
Figure 6:
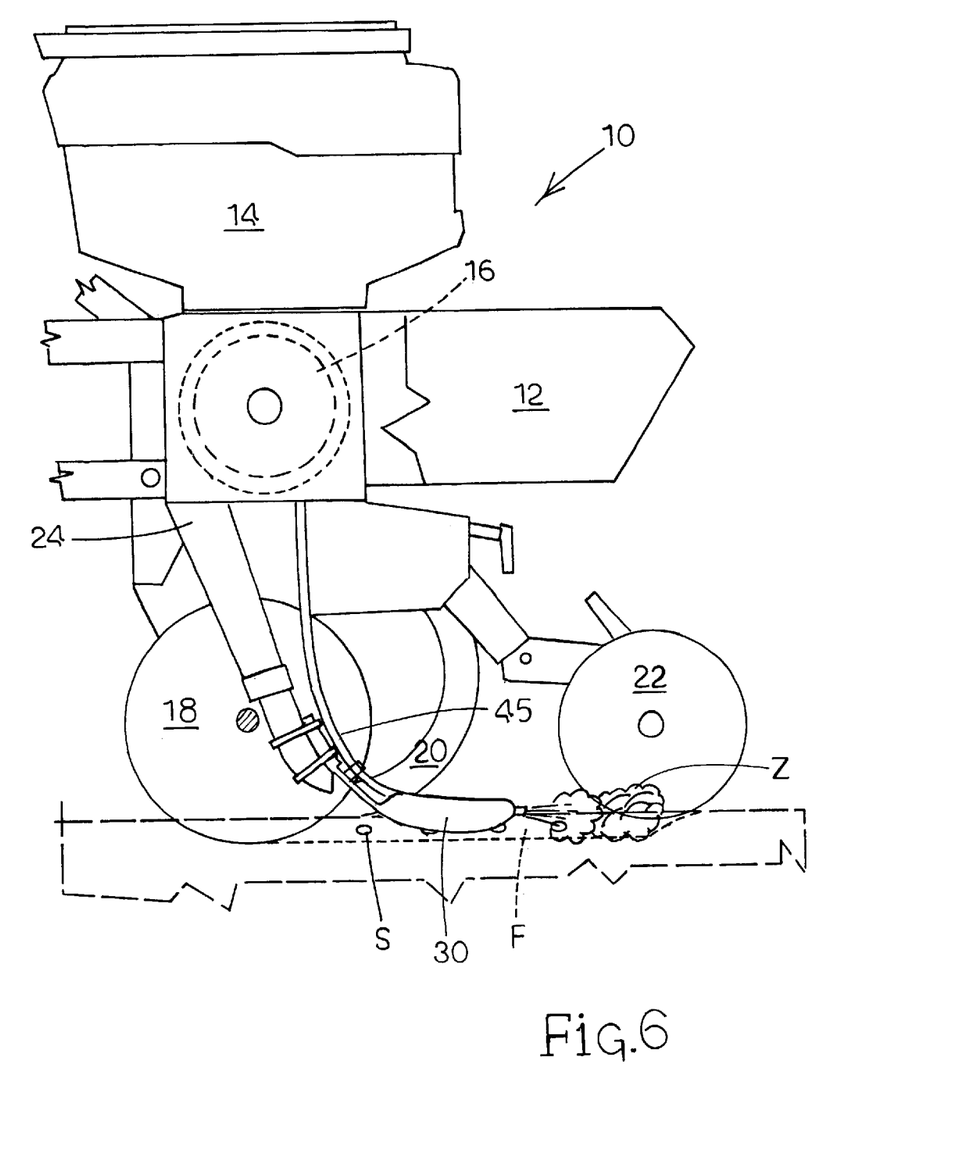
FIG. 6 is a side elevation view of a planting machine with a KEETON® seed firmer device being provided with a novel liquid pesticide delivery device.
Figure 7:
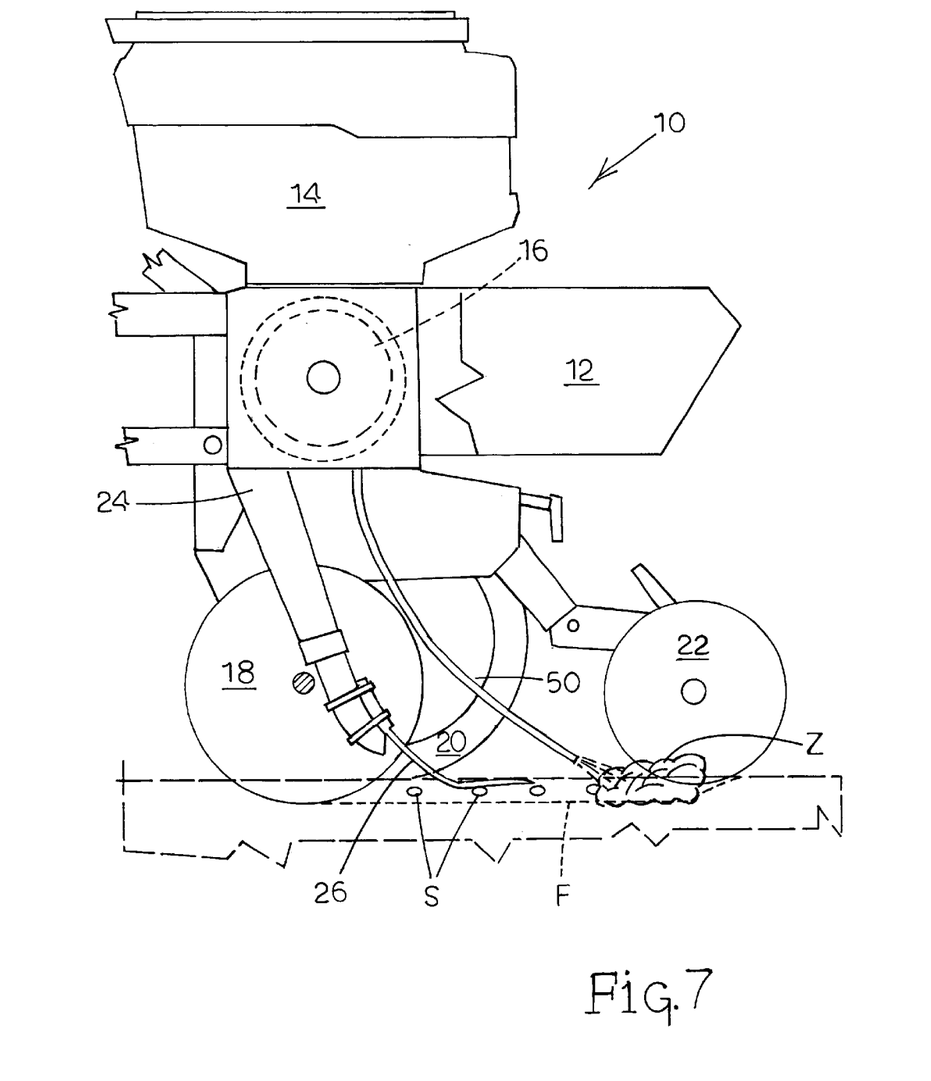
FIG. 7 is a side elevation view of a planting machine having a conventional REBOUNDER™ device for controlling seed attached to the seed tube and being further provided with a liquid pesticide delivery device in accordance with applicants' invention that is positioned between the seed tube and the furrow closing mechanism of the planting machine and which directs a liquid pesticidal composition into the soil mixing zone.

Applicants' invention can now be appreciated with reference to FIGS. 5–7 of the drawings. As seen in FIG. 5, applicants' liquid pesticide delivery tube 40 is used in combination with conventional planting machine 10 and REBOUNDER™ extension 26 attached to seed tube 24. Liquid pesticide delivery tube 40 in FIG. 5, however, is positioned on REBOUNDER™ extension 26 and provided with sufficient hydraulic pressure that the spray of liquid pesticide I carried therethrough will be directed downwardly and rearwardly into the soil mixing zone or dirt turbulence zone Z immediately in front of furrow closing device 22. Applicants have unexpectedly and surprisingly discovered that by introducing liquid pesticide I into the "zone of turbulence" (otherwise known as the soil mixing zone) being created at the leading edge of furrow closing device 22, an advantageous admixture of the liquid pesticide and soil can be created that will result in seed S being covered in furrow F with the admixture of soil and liquid pesticide as illustrated in FIG. 8C of the drawings. The introduction of liquid pesticide I into "zone of turbulence" Z being created by furrow closing device 22 in order to cover seed S in furrow F with a admixture of soil and liquid pesticide is highly desirable since the root ball above each of seeds S will be better protected from rootworm attack and the like. This is in contrast to the provision of only a minor coating of seed S with liquid pesticide I accomplished by the prior art and shown in FIG. 8A and FIG. 8B of the drawings.

A second embodiment of applicants invention is shown in FIG. 6 wherein liquid pesticide tube 45 is attached to KEETON® seed firmer 30 with the lowermost end thereof directed downwardly and rearwardly so as to deliver liquid pesticide I directly into the dirt turbulence or zone of turbulence Z being created immediately in front of furrow closing device 22. Applicants' improvement to prior art KEETON® seed firmer 30 (as shown in FIG. 4) results in an admixture of dirt and liquid pesticide being provided over seed S in furrow F as opposed to only the shallow coating of liquid fertilizer I to seed S as shown in prior art FIG. 8B.

Finally, a third embodiment of applicants' invention is shown in FIG. 7 wherein liquid pesticide tube 50 is provided between seed tube 24 and furrow closing device 22 and oriented generally downwardly and rearwardly so as to effectively apply liquid pesticide into zone of turbulence Z being created at the leading edge of furrow closing device 22 as furrow F is filled with soil in order to cover seed S. Liquid pesticide tube 50 (similarly to liquid pesticide tube 40 and 45 in FIGS. 5 and 6, respectively) is desirably positioned in a suitable orientation to assure that liquid pesticide from a reservoir (not shown) carried by planting machine 10 is introduced into zone of turbulence Z in front of furrow closing device 22.

Moreover, as a matter of design choice, liquid pesticide I is provided from the reservoir (not shown) carried by planting machine 10 by either gravity feed or mechanical pump feed so as to be under sufficient pressure to be suitably delivered into zone of turbulence Z by tubes 40, 45 and 50. The orientation of liquid pesticide tubes 40, 45 and 50 and the necessary delivery force to assure application to zone of turbulence Z is a matter of design choice and can be easily accomplished by one of skill in the art. Also, although for purposes of illustration the disclosure has referenced the insecticide fipronil applicants' invention is intended for application of a variety of liquid pesticides and any other liquids that are advantageously applied to seeds S in furrow F prior to being covered by furrow closing device 22 of planting machine 10 as heretofore described.

Applicants provide the following Examples to illustrate the invention.

EXAMPLE 1

Applicants utilized fluorescent dye to evaluate application of REGENT® liquid insecticide at about 0.13 lb of fipronil per acre in accordance with the prior art. A JOHN DEERE Model 7100 seed planter was utilized with (1) a KEETON® seed firmer (see FIG. 4) and (2) a Schaffert Manufacturing Company, Inc. REBOUNDER™ (see FIG. 3) seed positioner.

Applicants observed that the prior art KEETON® seed firmer in accordance with FIG. 4 placed liquid pesticide at a rate of about 1 gallon per acre directly on top of and slightly below seed S in a very concentrated band. The KEETON® configuration of FIG. 4 delivered the product about 14 inches behind where seed S was dropped by seed tube 24. The seed firmer pressed seed S to the very bottom of furrow F and excluded soil from dropping into the furrow until after the KEETON® seed firmer passed over seeds S. The liquid pesticide application result is shown in previously referenced prior art FIG. 8B.

Figure 8A:
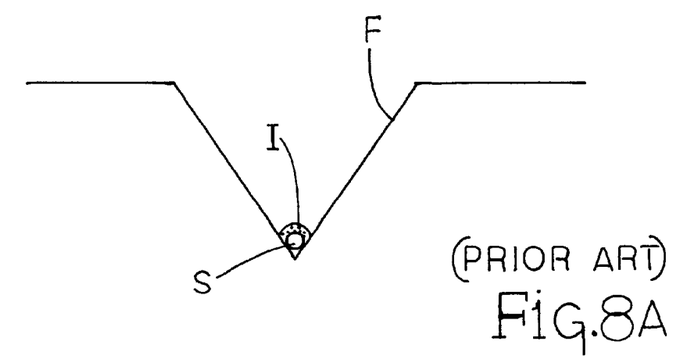
FIGS. 8A–8C are vertical cross-sectional views illustrating application of liquid pesticide to a seed within a furrow by the prior art device of FIGS. 1–4, and the applicants' invention as shown in FIGS. 5–7 of the drawings, respectively.
Figure 8B:
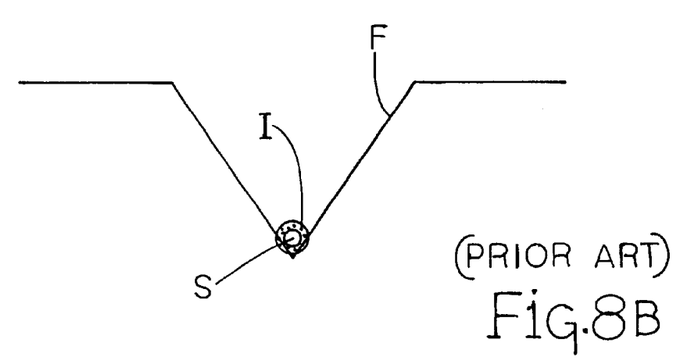
Figure 8C:
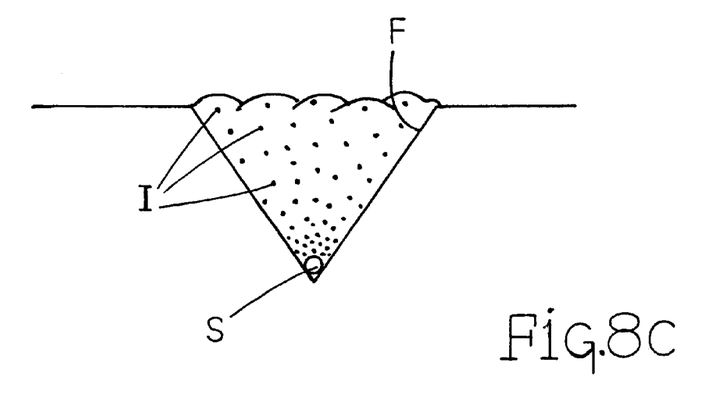

The prior art REBOUNDER™ device (see FIG. 3) placed liquid pesticide I at a rate of 1 gallon per acre above seed S as best shown in previously referenced prior art FIG. 8A. The majority of the liquid pesticide was placed from about ¼ inch above seed S to within ¼ to ½ inch of the soil surface for a modified in-furrow application. The REBOUNDER™ device delivered the liquid pesticide about 2 inches behind where seed S was dropped by seed tube 24. The seed firmer rubbed against the outer wall of furrow F to scrape a small amount of soil off the sidewall before sliding over seed S in furrow F.

When the above treatments are repeated with a soil about 50° F., there is feeding above the level of the seed placement in the soil resulting in damage to the crop.

EXAMPLE 2

The application of REGENT® of Example 1 is repeated using the following method in accordance with the present invention.

The apparatus of FIG. 5 provides a liquid insecticide spray (of REGENT®) angled at a preferred contact angle of about 25° relative to the ground and introduces liquid pesticide directly into the "zone of turbulence" in front of furrow closing device 22 to provide excellent mixing with soil introduced into furrow F. This allows for the most even distribution of liquid pesticide I above seeds S of the 3 referenced tests (see FIG. 8C). Although applicants' improved REBOUNDER™ seed firmer as shown in FIG. 5 was tested, applicants' second and third embodiments including improved KEETON® seed firmer as shown in FIG. 6 and the free tube embodiment 50 of applicants' invention as shown in FIG. 7 generally produce the same results as illustrated in FIG. 8C of the drawings.

The level of feeding by rootworms on roots of corn plants of Example 2 is less than that of Example 1. There is substantially no insecticide on or above the level of the soil.

It will be understood that various details of the invention may be changed without departing from the scope of the invention. Furthermore, the foregoing description is for the purpose of illustration only, and not for the purpose of limitation—the invention being defined by the claims.

What is claimed is:

1. A planting assembly having (i) a furrow opening mechanism, (ii) a seed dispenser, including a seed tube for directing seeds downwardly and rearwardly as the planting assembly moves forward, and (iii) a furrow closing mechanism that creates a soil mixing zone in front of a leading edge thereof, said assembly comprising:

(a) a liquid pesticide spray delivery device mounted on said planting assembly and directed towards the furrow closing mechanism, said spray delivery device adapted to provide sufficient force to apply the spray above and behind deposited seeds and rearwardly into the soil mixing zone.

2. The planting assembly according to claim 1, including seed guiding and positioning apparatus mounted on said seed tube for effectively placing seed at a desired location in the furrow.

3. The planting assembly according to claim 2, wherein said seed guiding and positioning apparatus is selected from the group comprising seed firmer devices and seed rebounder devices.

4. The planting assembly according to claim 2 or 3, wherein said liquid pesticide spray delivery device is a tube and said tube is mounted to said seed guiding and positioning apparatus so as to be directed generally rearwardly from said seed guiding and positioning apparatus into the soil mixing zone.

5. The planting assembly according to claim 1 or 2, wherein said liquid pesticide spray delivery device is a downwardly depending tube mounted on said planting assembly between said seed tube and said furrow closing mechanism so that a spray delivery end thereof is positioned forwardly of the soil mixing zone being created by said furrow closing mechanism where the spray delivery end will direct the pesticide spray above and behind deposited seeds and rearwardly into the soil mixing zone.

6. The planting assembly according to claim 5, wherein said downwardly depending tube extends rearwardly towards said furrow closing mechanism at a rearward angle of about 25° relative to the ground.

7. A method of application of liquid pesticide to a seed furrow created by a planting assembly having (i) a furrow opening mechanism, (ii) a seed dispenser, including a seed tube for directing seeds downwardly and rearwardly as the planting assembly moves forward, and (iii) a furrow closing mechanism that creates a soil mixing zone in front of a leading edge thereof, said method comprising the steps of:

(a) directing liquid pesticide spray with sufficient force to apply the spray above and behind deposited seeds and rearwardly into the soil mixing zone in front of said furrow closing mechanism; and (b) covering seed in the seed furrow with soil comprising the mixture of soil and liquid pesticide spray.

8. The method according to claim 7, wherein said planting assembly is provided with a seed guiding and positioning apparatus for positioning seeds in the furrow as seeds are deposited.

9. The method according to claim 7, wherein said planting assembly is provided with a liquid pesticide spray delivery device thereon.

10. The method according to claim 8, including mounting said liquid pesticide spray delivery device on said seed guiding and positioning apparatus.

11. The method according to claim 10, wherein said seed guiding and positioning apparatus comprises a seed firmer device.

12. The method according to claim 10, wherein said seed guiding and positioning apparatus comprises a seed rebounder device.

13. The method according to claim 7, including mounting said liquid pesticide spray delivery device between said seed guiding and positioning apparatus and said furrow closing mechanism.

* * * * *